United States Patent [19]

Heerdt et al.

[11] 3,996,241
[45] Dec. 7, 1976

[54] 2-HYDROXYMETHYL INDOLE COMPOUNDS AND BLOOD SUGAR LOWERING COMPOSITIONS

[75] Inventors: Ruth Heerdt, Mannheim-Feudenheim; Manfred Hübner, Ludwigshafen (Rhine); Felix Helmut Schmidt, Mannheim-Seckenheim; Kurt Stach, Mannheim-Waldhof, all of Germany

[73] Assignee: Boehringer Mannheim G.m.b.H., Mannheim-Waldhof, Germany

[22] Filed: Oct. 22, 1974

[21] Appl. No.: 516,947

[30] Foreign Application Priority Data

Nov. 27, 1973 Germany ............................ 2358973

[52] U.S. Cl. ............... 260/326.16; 260/326.13 R; 424/274
[51] Int. Cl.² ................................. C07D 209/12
[58] Field of Search .............. 260/326.16

[56] References Cited

UNITED STATES PATENTS 3,226,399   12/1965   Allen, Jr. et al. ............ 260/326.16

OTHER PUBLICATIONS

Bhat et al., J. Chem. Soc., vol. 1971, pp. 178–181 (1971).

Hirata et al., Tetrahedron Letters, 1969:(1), pp. 19–22 (1969).
Hosmane et al., J. Heterocyclic Chem. vol. 11(1), pp. 29–32 (2/74).

*Primary Examiner*—Lewis Gotts
*Assistant Examiner*—S. P. Williams
*Attorney, Agent, or Firm*—Burgess, Dinklage & Sprung

[57] ABSTRACT

New indole derivatives of the formula

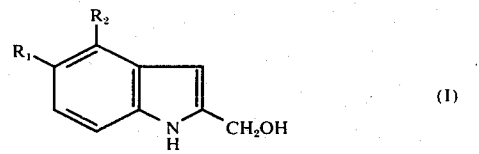

wherein
$R_1$ and $R_2$, which may be the same or different, are hydrogen or halogen or lower alkyl or, taken together, represent a —CH=CH-CH=CH— bridge, with the proviso that $R_1$ and $R_2$ are not both hydrogen, and wherein, when $R_2$ is halogen or alkyl, $R_1$ can also be alkoxy;
are outstandingly effective in blood sugar lowering action in mammals.

16 Claims, No Drawings

2-HYDROXYMETHYL INDOLE COMPOUNDS AND BLOOD SUGAR LOWERING COMPOSITIONS

The present invention relates to new indole compounds and to therapeutic uses and compositions thereof.

From the work of Bauman et al. (Biochemical Pharmacology, 18, 1241–1243/1969), it is known that 2-hydroxymethylindole exhibits a certain blood sugar-lowering action in rats but by no means achieves the strength of activity of 5-methoxyindole-2-carboxylic acid (MICA).

We have now found that a group of previously unknown 2-hydroxymethyl-indole derivatives substituted in the 4- and/or 5 position surprisingly show a stronger blood sugar-lowering action than the unsubstituted 2-hydroxymethyl-indole.

The present invention provides new indole derivatives of the formula:

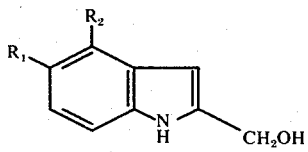

(I)

wherein
$R_1$ and $R_2$, which may be the same or different, are hydrogen or halogen or lower alkyl or,
taken together, represent a $-CH=CH-CH=CH-$ bridge, with the proviso that $R_1$ and $R_2$ are not both hydrogen, and wherein, when $R_2$ is halogen or alkyl, $R_1$ can also be alkoxy.

By lower alkyl and alkoxy radicals, within the scope of the present invention, there are to be understood radicals containing up to 5 and preferably up to 2 carbon atoms. Halogen is to be understood to mean chlorine, bromine or fluorine, chlorine and bromine being preferred.

Apart from the compounds specifically mentioned in the following Examples, the present invention also includes all compounds which have every possible combination of the substituents mentioned in the Examples.

The new compounds according to the present invention can be prepared by the processes known from the literature but preferably either by a. treating an indole derivative of the general formula:

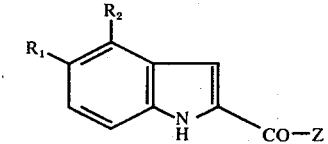

(II)

wherein $R_1$ and $R_2$ have the same meanings as above and Z is a hydroxyl group or an alkoxy or acyloxy radical or a hydrogen or halogen atom, with a suitable reduction agent; or b. treating an indole derivative of the general formula:

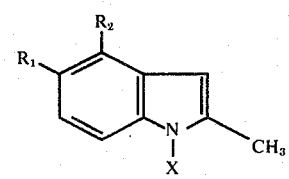

(III)

wherein $R_1$ and $R_2$ have the same meanings as above and X is a hydrogen atom or a protective group, with a suitable oxidation agent, whereafter, if necessary, the protective group X is split off and/or a derivative of the hydroxymethyl-indole possibly formed initially is converted into the corresponding free hydroxymethyl compound.

The protective group X can be, for example, an acyl radical.

The starting materials of general formula (II) can be obtained in known manner, preferably according to the so-called Reissert Synthesis or the Fischer synthesis, whereby the initially formed carboxylic acids or esters are possibly converted in known manner into the corresponding acid chlorides, anhydrides or aldehydes.

As reduction agent, there is preferably used a complex metal hydride, for example lithium aluminium hydride, sodium aluminium hydride, sodium borohydride or also diborane, whereas the reduction with metals, for example with sodium according to the Bouveault-Blanc method, is less suitable. The compounds of general formula (I), insofar as they do not contain halogen atoms as substituents $R_1$ and/or $R_2$, can also be prepared by catalytic hydrogenation.

The starting materials of general formula (III) can be obtained by means of the many processes developed for the synthesis of indole derivatives, the methods of Fischer, Madelung and Bischler being especially suitable.

As oxidation agent, there can be used, for example, lead tetraacetate in glacial acetic acid; the acetyl derivative initially formed can be saponified with alkalis. The methyl radical can also be converted with a halogen, preferably bromine, via an intermediate halogen compound, into a hydroxymethyl radical.

The following Examples are given for the purpose of illustrating, without limitation, the present invention:

EXAMPLE 1

Preparation of 5-Methoxy-4-methyl-2-hydroxymethylindole 50 ml. anhydrous diethyl ether and 0.8 g. lithium aluminium hydride were placed in a 500 ml. three-necked flask equipped with a stirrer, dropping funnel and reflux condenser provided with a calcium chloride tube. A solution of 4.65 g. ethyl 5-methoxy-4-methylindole-2-carboxylate in 150 ml. anhydrous diethyl ether was added dropwise thereto, while stirring at ambient temperature, within the course of about 30 minutes. Thereafter, the reaction mixture was heated under reflux for 1 hour. After cooling, 15 ml. water were slowly added dropwise and precipitated inorganic compounds were filtered off with suction and then thoroughly washed out with diethyl ether. The combined ethereal solutions were dried with anhydrous magnesium sulphate and then evaporated to dryness. Finally, the product was recrystallized from toluene, with the use of active charcoal. There were obtained 3.4 g.

(89% of theory) 5-methoxy-4-methyl-2-hydroxymethyl-indole, which had a melting point of 133° – 135° C.

The following compounds were prepared in an analogous manner:

4-methyl-2-hydroxymethyl-indole; m.p. 68° – 70° C., after recrystallization from tetrahydrofuran;

5-ethyl-2-hydroxymethyl-indole; m.p. 96° – 98° C., after recrystallization from toluene;

4-chloro-2-hydroxymethyl-indole; m.p. 69° –70° C., after recrystallization from carbon tetrachloride 5-bromo-2-hydroxymethyl-indole; m.p. 112° – 116° C., after recrystallization from toluene;

2-hydroxymethyl-3H-benzo [e] indole; m.p. 131° –133° C., after recrystallization from toluene; and 5-ethoxy-4-methyl-2-hydroxymethyl-indole; m.p. 152° –154° C., after recrystallization from toluene.

EXAMPLE 2

Preparation of 5-Chloro-4-methyl-2-hydroxymethylindole 240 ml. anhydrous tetrahydrofuran and 3.5 g. lithium aluminium hydride were placed in a 1 liter three-necked flask equipped with a stirrer, dropping funnel and reflux condenser provided with a calcium chloride tube. A solution of 6.5 g. 5-chloro-4-methyl-indole-2-carboxylic acid in 100 ml. anhydrous tetrahydrofuran was then slowly added thereto dropwise, while stirring at ambient temperature, whereafter the reaction mixture was heated to 50° C. for 2 hours. After cooling, 4.7 ml. water were added very slowly and carefully thereto dropwise and precipitated inorganic compounds were filtered off with suction and then thoroughly washed with tetrahydrofuran. The combined solutions were evaporated and the oily residue was dissolved in a little diethyl ether, mixed with ligroin and, after rubbing with a glass rod, brought to crystallization. There were thus obtained 3.6 g. (59% of theory) 5-chloro-4-methyl-2-hydroxymethyl-indole which can be recrystallized from toluene, with the use of active charcoal. The product had a melting point of 108° C.

EXAMPLE 3

Preparation of 4,5-Dimethyl-2-hydroxymethyl-indole 10.0 g. ethyl 4,5-dimethylindole-2-carboxylate were reduced with 6.1 g. lithium aluminium hydride in a total of 550 ml. tetrahydrofuran in the same way as is described in Example 2. After evaporation of the tetrahydrofuran, the residue was recrystallized from ethyl acetate. There were obtained 3.2 g. (40% of theory) 4,5-dimethyl-2-hydroxymethylindole, which had a melting point of 159° C.

In an analogous manner, there was obtained 5-methyl-2-hydroxymethyl-indole which, after recrystallization from toluene, had a melting point of 94° – 95° C.

EXAMPLE 4

Preparation of 4-Chloro-2-hydroxymethyl-indole 3.6 g 4-chloroindole-2-carbaldehyde, dissolved in 200 ml. anhydrous diethyl ether, were reduced with 1.0 g. lithium aluminium hydride in a further 50 ml. anhydrous diethyl ether in the manner described in Example 1 and the reaction mixture was then worked up in an analogous manner. The crude product obtained by evaporation of the ether was recrystallized from carbon tetrachloride, with the use of active charcoal. There were obtained 2.6 g. (71% of theory) 4-chloro-2-hydroxymethylindole, which had a melting point of 68° – 70° C.

As noted above, the compounds of the invention possess strong blood-sugar lowering action and can be formulated into therapeutic compositions.

The present invention also provides pharmaceutical compositions comprising at least one of the new compounds, in admixture with a solid or liquid pharmaceutical diluent or carrier. These compositions can be in the form of, for example, tablets, capsules, dragees, syrups, solutions, suspensions, drops, suppositories or the like. For this purpose, the active material is mixed with the solid or liquid pharmaceutical diluent or carrier and then brought into the desired form. Solid carrier materials include, for example, starch, lactose, mannitol, methyl cellulose, talc, highly-dispersed silic acid, high molecular weight fatty acids (for example stearic acid), gelatine, agar-agar, calcium phosphate, magnesium stearate, animal and vegetable fats and solid high molecular weight polymers (for example polyethylene glycols). Compositions suitable for oral administration can, if desired, contain flavoring and/or sweetening agents.

The blood sugar-lowering effectiveness of the indolecarboxylic acids according to the present invention was tested on rats and compared with 2-hydroxymethyl-indole and 5-methoxy (and 5-ethoxy)-2-hydroxymethyl-indole as conventional substances (Chem. Abstr. 70, 77690 c; 71, 12941 m; 74, 53406 w).

The test compounds were administered as a solution in tylose to fasting male Sprague-Dawley rats with a body weight of 200–220 g. via a stomach tube. In the following Table 1, there is given the threshold dose which significantly lowers the blood sugar level and from this value was calculated the relative effectiveness, referred to 2-hydroxymethyl-indole which was assigned an effectiveness rating of 1.

| Test Compound | Threshold Dosage | Relative Effectiveness |
| --- | --- | --- |
| 4-Methyl-2-hydroxymethyl-indole | 5 mg/kg | 10 |
| 5-Bromo-2-hydroxymethyl-indole | 20 mg/kg | 2.5 |
| 5-Chloro-4-methyl-2-hydroxymethyl-indole | 10 mg/kg | 5 |
| 5-Methoxy-4-methyl-2-hydroxymethyl-indole | 10 mg/kg | 5 |
| 4,5-Dimethyl-2-hydroxymethyl-indole | 20 mg/kg | 2 |
| 5-Ethoxy-4-methyl-2-hydroxymethyl-indole | 20 mg/kg | 2.5 |
| 2-Hydroxymethyl-indole | 50 mg/kg | 1 |
| 5-Methoxy-2-hydroxymethyl-indole | 30 mg/kg | 1.7 |
| 5-Ethoxy-2-hydroxymethyl-indole | 60 mg/kg | & none |

While the method of administering the active ingredients of the novel compositions of matter of the present invention is not limited to oral administration, a decided advantage of the present invention is that the active ingredients may be administered orally in any convenient manner. They may be taken orally for example, with an inert diluent or with an assimilable edible carrier, or they may be compressed into tablets, or enclosed in hard or soft gelatin capsules. Furthermore, the active ingredients may be administered either individually or as mixtures of a plurality of such active ingredients. The amounts of a single dose or of a daily dose necessary to induce a particular level of hypoglycemia will vary with the size or weight of the warm-blooded animal to be treated.

Generally, it should be such as to give a proportionate dosage of from about 2.5 mg to about 25 mg per kg of body weight per day of, for example, 5-methoxyindole-2-carboxylic acid, a highly active compound, or other active ingredient or mixture thereof. In terms of total weight of active ingredient, the daily dosage for warm-blooded animals of, for example, 75 kilograms, would amount to from about 0.1 g to about 2.0 g. The dosage regimen may be adjusted to provide optimum therapeutic response; for example, several divided doses may be administered daily or the dose may be proportionately reduced or increased as the requirements of the therapeutic situation would indicate.

It will be understood that the specification and examples are illustrative but not limitative of the present invention and that other embodiments within the spirit and scope of the invention will suggest themselves to those skilled in the art.

What is claimed is:

1. Indole compound of the formula

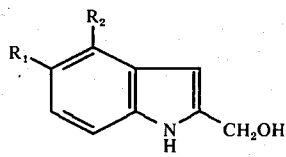

(I)

wherein $R_1$ is hydrogen, halogen, lower alkyl or lower alkoxy $R_2$ is hydrogen, halogen, or lower alkyl with the proviso that $R_1$ and $R_2$ be not both hydrogen, and wherein, when $R_1$ is alkoxy, $R_2$ is halogen or alkyl; and $R_1$ and $R_2$ taken together, represent a —CH=CH—CH=CH—bridge.

2. Indole compound as claimed in claim 1 wherein $R_1$ is hydrogen and $R_2$ is halogen or alkyl.

3. Indole compound as claimed in claim 1 wherein $R_2$ is hydrogen and $R_1$ is halogen or alkyl.

4. Indole compound as claimed in claim 1 wherein $R_1$ is halogen.

5. Indole compound as claimed in claim 1 wherein $R_2$ is halogen.

6. Indole compound as claimed in claim 1 wherein $R_2$ is alkyl.

7. Indole compound as claimed in claim 1 wherein $R_2$ is alkyl.

8. Indole compound as claimed in claim 1 wherein $R_1$ and $R_2$ taken together represent a -CH=CH-CH=CH- bridge.

9. Indole compound as claimed in claim 1 wherein $R_2$ is halogen and $R_1$ is alkoxy.

10. Indole compound as claimed in claim 1 wherein $R_2$ is alkyl and $R_1$ is alkoxy.

11. Indole compound as claimed in claim 1 designated 5-methoxy-4-methyl-2-hydroxymethyl-indole.

12. Indole compound as claimed in claim 1 designated 4-methyl-2-hydroxymethyl-indole.

13. Indole compound as claimed in claim 1 designated 5-bromo-2-hydroxymethyl-indole.

14. Indole compound as claimed in claim 1 designated 5-ethoxy-4-methyl-2-hydroxymethyl-indole.

15. Indole compound as claimed in claim 1 designated 5-chloro-4-methyl-2-hydroxymethyl-indole.

16. Indole compound as claimed in claim 1 designated 4,5-dimethyl-2-hydroxymethyl-indole.

* * * * *